United States Patent [19]

Nutt et al.

[11] Patent Number: 5,374,622
[45] Date of Patent: Dec. 20, 1994

[54] FIBRINOGEN RECEPTOR ANTAGONISTS

[75] Inventors: Ruth F. Nutt, Green Lane; Stephen F. Brady, Philadelphia; Daniel F. Veber, Ambler; Mark E. Duggan, Narberth, all of Pa.

[73] Assignee: Merck & Co., Inc., Rahway, N.J.

[21] Appl. No.: 10,234

[22] Filed: Jan. 28, 1993

Related U.S. Application Data

[60] Division of Ser. No. 989,738, Dec. 10, 1992, which is a continuation of Ser. No. 421,049, Oct. 13, 1989, abandoned.

[51] Int. Cl.$^5$ .............................. A61K 37/02
[52] U.S. Cl. ........................ 514/16; 530/329
[58] Field of Search ............... 514/16; 530/317, 329

[56] References Cited

U.S. PATENT DOCUMENTS

| | | | |
|---|---|---|---|
| 4,559,324 | 12/1985 | Fujino | 514/14 |
| 4,772,686 | 9/1988 | Szelke | 530/331 |
| 4,857,508 | 8/1989 | Adams | 514/18 |
| 4,952,562 | 8/1990 | Klein | 514/18 |
| 4,988,621 | 1/1991 | Ruoslahti | 435/240.2 |

FOREIGN PATENT DOCUMENTS

| | | |
|---|---|---|
| 275748 | 7/1988 | European Pat. Off. ...... C07K 7/06 |
| 0341915 | 11/1989 | European Pat. Off. ...... C07K 5/00 |
| 0406428 | 1/1991 | European Pat. Off. ...... C07K 5/12 |
| 0425212 | 5/1991 | European Pat. Off. ...... C07K 7/02 |
| 8905150 | 6/1989 | WIPO ...... A61K 37/02 |

OTHER PUBLICATIONS

Ramjit *J Pharm Exp Ther* 266, 1501, 1993.
Plow, *Proc Natl Acad Sci* 82, 8057, 1985.
Rose, *Adv Prot Chem* 37, 19-45, 1985.
Smith *J Med Chem* 21, 117, 1978.
Pierschbacher *Proc Natl Acad Sci* 81, 5985-5988, 1984.
Nutt, *Peptides, Struct and Funct* 441-444, 1985.
Hase *J Am Chem Soc* 94, 3590, 1972.
Progress in Drugs Research (1966) pp. 508-509, Ariens et al.
J. Biol. Chem. (1987), 262 (86) pp. 17294-17298 (A) Influence of Stereochemistry, Pierschbacher et al.

*Primary Examiner*—Robert J. Hill, Jr.
*Assistant Examiner*—David Lukton
*Attorney, Agent, or Firm*—Richard S. Parr; Melvin Winokur; Paul D. Matukaitis

[57] ABSTRACT

A fibrinogen receptor antagonist of the formula

Ac-Cys-Asn-Pro-(L-AMF)-Gly-Asp-Cys-OH or

Ac-Cys-Asn-(DiMeTzl)-(L-AMF)-Gly-Asp-Cys-OH.

3 Claims, No Drawings

FIBRINOGEN RECEPTOR ANTAGONISTS

This is a division of application Ser. No. 07/989,738 as filed on Dec. 10, 1992 which is a continuation of application Ser. No. 07/421,049, filed on Oct. 13, 1989; now abandoned.

BACKGROUND OF THE INVENTION

This invention relates to compounds for inhibiting the binding of fibrinogen to blood platelets, and for inhibiting the aggregation of blood platelets.

Fibrinogen is a glycoprotein, present in blood plasma, which participates in platelet aggregation and fibrin formation. Platelets are cell-like anucleated fragments, found in the blood of all mammals, which participate in blood coagulation. Interaction of fibrinogen with a receptor on the platelet membrane glycoprotein complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood. The general formula for the peptides is:

H$_2$N-(Ch)-Arg-Gly-Asp-(Cx)-H where Ch and Cx are sequences of amino acids.

Pierschbacher et al., U.S. Pat. No. 4,589,881, describes the sequence of an 11.5 kDal polypeptide fragment of fibronectin which embodies the cell-attachment-promoting activity of fibronectin. A specifically described fragment is:

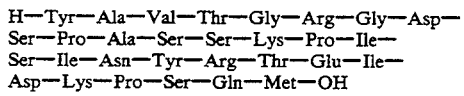

H—Tyr—Ala—Val—Thr—Gly—Arg—Gly—Asp—
Ser—Pro—Ala—Ser—Ser—Lys—Pro—Ile—
Ser—Ile—Asn—Tyr—Arg—Thr—Glu—Ile—
Asp—Lys—Pro—Ser—Gln—Met—OH

Ruoslahti et al., U.S. Pat. No. 4,614,517, describes tetrapeptides which alter cell-attachment activity of cells to various substrates. The peptides are stated to "consist essentially of" the following sequence:

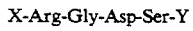

X-Arg-Gly-Asp-Ser-Y wherein X is H or one or more amino acids and Y is OH or one or amino acids. FIG. 1 lists the polypeptides that were synthesized by Ruoslahti et al. in "determining the smallest peptide exhibiting cell attachment activity".

Ruoslahti et al., U.S. Pat. No. 4,578,079, describes similar tetrapeptides having Ser substituted with Thr or Cys.

Pierschbacher et al., Proc. Natl. Acad. Sci. USA, Vol. 81, pp.5985–5988, October 1984 describe variants of the cell recognition site of fibronectin that retain attachment-promoting activity. They assayed the cell attachment-promoting activities of a number of structures closely resembling the Arg-Gly-Asp-Ser peptide, and found "that the arginine, glycine, and aspartate residues cannot be replaced even with closely related amino acids, but that several amino acids can replace serine without loss of activity."

Ruoslahti et al., Science, Vol. 238, pp. 491–497, Oct. 23, 1987, discuss cell adhesion proteins. They specifically state that "[e]lucidation of the amino acid sequence of the cell-attachment domain in fibronectin and its duplication with synthetic peptides establish the sequence Arg-Gly-Asp (RGD) as the essential structure recognized by cells in fibronectin".

Cheresh, Proc. Natl. Acad. Sci. USA, Vol. 84, pp. 6471–6475, September 1987, describes the Arg-Gly-Asp-directed adhesion receptor involved in attachment to fibrinogen and von Willebrand Factor.

Adams et al., U. S. Pat. No. 4,857,508, describes tetrapeptides which inhibit platelet aggregation and the formation of a thrombus. The tetrapeptides have the formula:

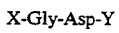

X-Gly-Asp-Y wherein X can be H2NC(=NH)NH(CH2)nCH(Z)COOH or Ac-Arg, wherein Z=H, NH2, or NH-Acyl and n=1–4, and wherein Y can be Tyr-NH2, Phe-NH2 or a group of a specifically defined formula.

Applicants have discovered fibrinogen receptor antagonists which do not contain the amino acid sequence Arg-Gly-Asp which is taught in the art as specifically required for binding to platelet membrane glycoprotein complex IIb/IIIa.

SUMMARY OF THE INVENTION

Compounds of the present invention inhibit binding of fibrinogen to the platelet membrane glycoprotein complex IIb/IIIa receptor and contain an amino acid sequence:

XX-Gly-Asp wherein XX is a synthetic alpha amino acid containing either a phenyl or C$_3$–C$_8$ cycloalkyl group. These compounds are surprising in view of the prior art which teaches that the sequence Arg-Gly-Asp is required in order to achieve binding to the IIb/IIIa receptor.

The present invention is a fibrinogen receptor antagonist having the following structure:

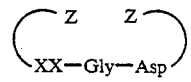

wherein XX represents a synthetic α-amino acid as defined below and ZZ represents a sequence of 1, 2, 3, or 4 amino acids as defined below.

XX shares an amide bond with Gly and an amide bond with ZZ, and is defined as having a side chain X

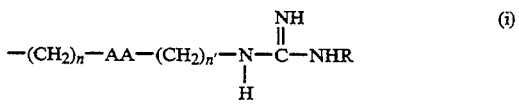

—(CH$_2$)$_n$—AA—(CH$_2$)$_{n'}$—N—C—NHR    (i)
                              |    ||
                              H    NH or

—(CH$_2$)$_n$—AA—(CH$_2$)$_{n'}$—NHR    (ii)

wherein:
n is 0, 1, 2, 3 or 4;
n' is 0, 1, 2, 3 or 4;
AA is disubstituted phenyl, either not substituted with additional groups or substituted with C$_{1-4}$ alkyl, alkoxy or hydroxy; C$_3$–C$_8$ cycloalkyl, preferably cyclohexyl, either not substituted with additional groups or substituted with $C_{1-4}$ alkyl, alkoxy or hydroxy; and R is H, $C_{1-6}$ alkyl, substituted or unsubstituted aryl, substituted or unsubstituted arylmethyl or substituted or unsubstituted cycloalkyl.

Preferably, the side chain of XX is defined by (ii) wherein n is 1, n' is 1, AA is unsubstituted phenyl and R is H. More preferably, the side chain is

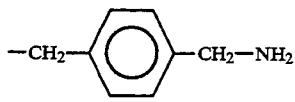

where xx is p-aminomethylphenylalanine.

Also preferred is the side chain of XX defined by (ii) wherein n is 1, n' is O, R is H and AA is unsubstituted cyclohexyl. More preferably, the side chain is

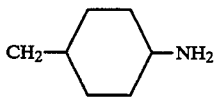

Preferred compounds of the invention are those having selectivity over integrin receptors. The preferred compounds include those wherein XX is a synthetic alpha-amino acid containing an amino group side chain, as represented above by (ii).

ZZ is defined as follows:

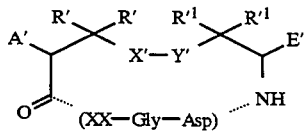

wherein:
- A' is H, acylamido, acylaminoacylamido, acylamino-N-methylamino-acylamido;
- R' and R'¹ are independently H, methyl, ethyl or a lower alkyl group having 1 to 5 carbons;
- X'—Y' is S—S, $CH_2$—S, S—$CH_2$, $CH_2CH_2$, $CH_2$, $CH_2CH_2CH_2$, $CH_2$—S—S, $CH_2$—S—S—$CH_2$, S—S—$CH_2$; and
- E' is H, COOH, $CONH_2$, $CONHR^2$, $CONR^3R^4$, $CH_2OH$, $CO_2R^2$, $CH_3$ wherein $R^2$ is an alkyl group having 1 to 4 carbon atoms, $R^3R^4$ is an alkyl group having 1 to 4 carbon atoms or $NR^3R^4$ is a secondary amino acid, or

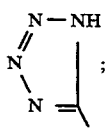

or ZZ is

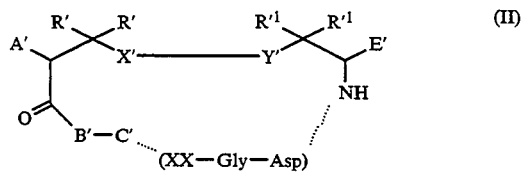

wherein:
- A' is as defined above;
- R' and R'¹ are as defined above;
- X'—Y' is as defined above;
- B' is a D- or L-α-amino acid;
- C' is a D- or L-secondary α-amino acid, preferably selected from proline, β-methylproline, β,β-dimethylproline, γ-hydroxyproline, anhydroproline, thioproline, γ-methylthioproline, β,β-dimethylthioproline, pipecolic acid, azetidine carboxylic acid and an N-methyl amino acid, or a D- or L-primary α-amino acid; and
- E' is as defined above;

or ZZ is

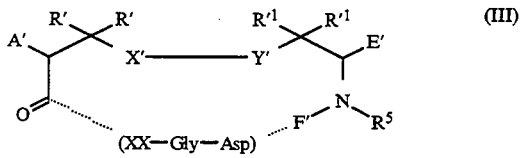

wherein:
- A' is as defined above;
- R' and R'¹ are as defined above;
- X'—Y' are as defined above;
- E' is as defined above;
- F' is an L-amino acid, preferably selected from tryptophan, phenylalanine, leucine, valine, isoleucine, α-naphthylalanine, β-naphthylalanine, methionine, tyrosine, arginine, lysine, homoarginine, ornithine, histidine, substituted tryptophan, substituted phenylalanine or substituted tyrosine; and $R^5$ is H or methyl;

or ZZ is

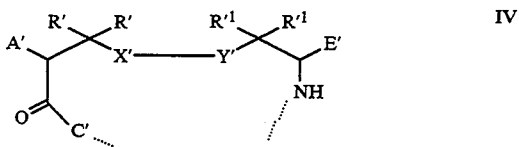

wherein
- A' is as defined above;
- R' and R'¹ are as defined above;
- X'—Y' is as defined above;
- C' is as defined above; and
- E' is as defined above.

or ZZ is

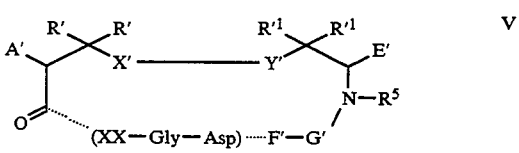

wherein

A' is as defined above;
R' and R'¹ are as defined above;
X'—Y' is as defined above;
F' is as defined above;
G' is a D- or L-α-amino acid, secondary cyclic amino acid, or N-methyl amino acid;
E' is as defined above; and
R⁵ is as defined above.

The present invention also is a fibrinogen receptor antagonist of the formula

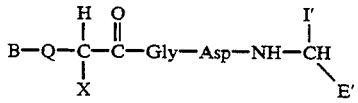

wherein:
- B represents zero one or two substituted or unsubstituted amino acids;
- Q represents H, NH, NH₂ or Ac—NH;
- X represents the side chain of amino acid XX as previously defined; and
- I' is a side chain of an amino acid previously defined by F', and
- E' is H, COOH, CONH₂, CONHR², CONR³R⁴, CH₂OH, CO₂R², CH₃ wherein R² is an alkyl group having 1 to 4 carbon atoms, R³R⁴ is an alkyl group having 1 to 4 carbon atoms or NR³R⁴ is a secondary amino acid, or

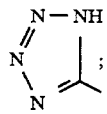

provided that when B is zero substituted or unsubstituted amino acids, then Q is H, NH₂ or Ac—NH, and that when B is one or two substituted or unsubstituted amino acids, then Q is NH.

In a preferred embodiment of the present invention, the fibrinogen receptor antagonist has the following formula:

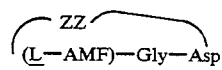

wherein ZZ is:

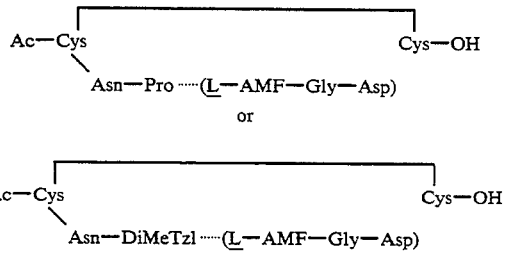

Exemplary compounds of the invention are:

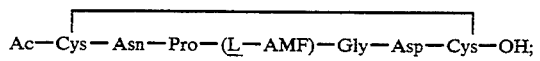

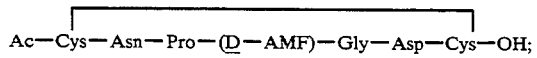

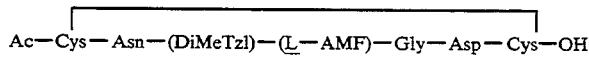

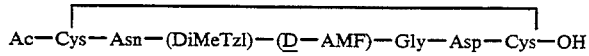

c(Aha—(L—AMF)—Gly—Asp—Trp—Pro);
c(Aha—(D—AMF)—Gly—Asp—Trp—Pro);

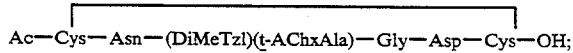

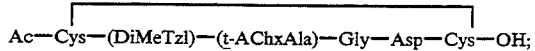

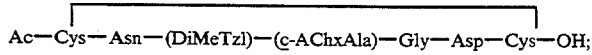

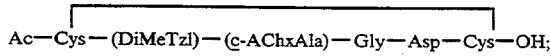

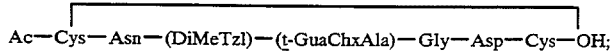

Ac—Cys—(DiMeTzl)—(t-GuaChxAla)—Gly—Asp—Cys—OH;

Ac—Cys—(DiMeTzl)—(c-GuaChxAla)—Gly—Asp—Cys—OH;

Ac—Cys—(DiMeTzl)—(c-GuaChxAla)—Gly—Asp—Cys—OH;

Ac—Cys—Asn—(DiMeTzl)—(t-AChxGly)—Gly—Asp—Cys—OH;

Ac—Cys—Asn—(DiMeTzl)——(t-GuaChxGly)—Gly—Asp—Cys—OH;

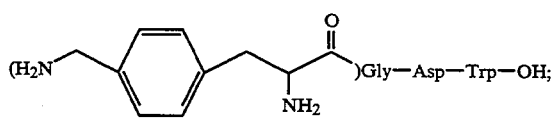)Gly—Asp—Trp—OH;

(L—AMF)

(D—AMF)—Gly—Asp—Trp—OH;
(D—t-AChxAla)—Gly—Asp—Trp—OH;
(L—t-AChxAla)—Gly—Asp—Trp—OH;
(D—c-AChxAla)—Gly—Asp—Trp—OH;
(L—c-AChxAla)—Gly—Asp—Trp—OH;
(D—t-GuaChxGly)—Gly—Asp—Trp—OH;
(L—t-GuaChxGly)—Gly—Asp—Trp—OH;
(D—c-GuaChxGly)—Gly—Asp—Trp—OH;
(L—c-GuaChxGly)—Gly—Asp—Trp—OH;

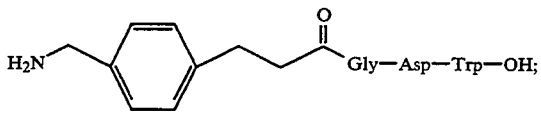Gly—Asp—Trp—OH;

Ac—Cys—AMF—Gly—Asp—Cys—OH;

Ac—Cys—(c-AChxAla)—Gly—Asp—Cys—OH;

Ac—Cys—(t-AChxAla)—Gly—Asp—Cys—OH;

Ac—Pen—AMF—Gly—Asp—Cys—OH;

Ac—Cys—AMF—Gly—Asp—Trp—(N—MeCys)—OH;

Ac—Cys—(c-AChxAla)—Gly—Asp—Trp—(N—MeCys)—OH;

Ac—Cys—(t-AChxAla)—Gly—Asp—Trp—(N—MeCys)—OH;

Ac—Cys—(DiMeTzl)—AMF—Gly—Asp—Cys—OH;

Ac—Cys—(DiMeTzl)—(c-AChxAla)—Gly—Asp—Cys—OH;

Ac—Cys—(DiMeTzl)—(t-AChxAla)—Gly—Asp—Cys—OH;

Ac—Cys—AMF—Gly—Asp—Trp—Pro—Cys—NH₂;

c(Aha—AMF—Gly—Asp—Trp—Pro);
c(Ahex—AMF—Gly—Asp—Trp—Pro);
c(Aha—(c-AChxAla)—Gly—Asp—Trp—Pro);
c(Ahex—(c-AChxAla)—Gly—Asp—Trp—Pro);
c(Aha—(t-AChxAla)—Gly—Asp—Trp—Pro);
c(Ahex—(t-AChxAla)—Gly—Asp—Trp—Pro);
c(Aha—(c-GuaChxGly)—Gly—Asp—Trp—Pro);
c(Ahex—(c-GuaChxGly)—Gly—Asp—Trp—Pro);
c(Aha—(t-GuaChxGly)—Gly—Asp—Trp—Pro);
c(Ahex—(t-GuaChxGly)—Gly—Asp—Trp—Pro);

Ac—Cys—Asn—(DiMeTzl)—(c-AChxGly)—Gly—Asp—Cys—OH;

and

Ac—Cys—Asn—(DiMeTzl)—(c-GuaChxGly)—Gly—Asp—Cys—OH;

Preferred compounds are:

Ac—Cys—Asn—Pro—(L—AMF)—Gly—Asp—Cys—OH;

Ac—Cys—Asn—(DiMeTzl)—(L—AMF)—Gly—Asp—Cys—OH;

Ac—Cys—Asn—(DiMeTzl)—(c-AChxAla)—Gly—Asp—Cys—OH;

c(Aha—(L—AMF)—Gly—Asp—Trp—Pro);

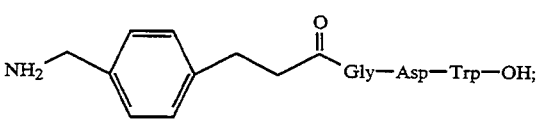Gly—Asp—Trp—OH;

and

Ac—Cys—Asn—(DiMeTzl)—(t-AChxAla)—Gly—Asp—Cys—OH.

In addition to the common three letter abbreviations used to identify common amino acids, applicants have used the following abbreviation designations:

| | |
|---|---|
| AMF | aminomethyl phenylalanine |
| t-AChxAla | trans-aminocyclohexylalanine |
| c-AChxAla | cis-aminocyclohexylalanine |
| t-AChxGly | trans-aminocyclohexylglycine |
| c-AChxGly | cis-aminocyclohexylglycine |
| GuaChxAla | guanidocyclohexylalanine |
| GuaChxGly | Guanidocyclohexylglycine |
| DiMeTzl | Dimethylthioproline |
| Aha | 7-NH₂ heptanoic acid |
| Ahex | 6-NH₂ hexanoic acid |

The invention also includes compositions, comprising fibrinogen receptor antagonist peptides of the present invention and one or more pharmacologically acceptable carriers, e.g. saline, at a pharmacologically acceptable pH, e.g. 7.4, which are suitable for continuous intravenous or oral or intravenous bolus administration for promoting inhibition of platelet aggregation.

The invention also includes methods for inhibiting platelet aggregation which comprise administering to a patient, either by continuous intravenous or oral or intravenous bolus method, an effective amount of a composition of the present invention.

DETAILED DESCRIPTION OF THE INVENTION

Compounds of the invention are fibrinogen receptor antagonists which inhibit fibrinogen induced platelet aggregation. These compounds are prepared by solid phase synthesis which is well known in the art, or by liquid method well known in the art (Neurath, Hill & Boeder, Eds. "The Proteins" 3rd Edition, Vol. II, Academic Press, 1976).

The compounds of the invention are specifically useful for preventing formation of blood clots by inhibiting the binding of fibrinogen to the platelet membrane glycoprotein complex IIb/IIIa receptor. Preferred compounds have selectivity over other integrin receptors, and thus are specifically designed for preventing thrombosis.

The procedures for synthesizing synthetic amino acids defined by XX are well know in the art.

PEPTIDES, Structure and Function, Pierce Chemical Company (Rockford, Ill.) (1985), Deber et al. Eds, Nutt et al., "Novel Conformationally Constrained Amino Acids as Lysine-9 Substitutions in Somatostatin Analogs: pp. 441–444, describe procedures for preparing cis- and trans-4-aminocyclohexylglycine (AChxGly), cis- and trans-4-aminocyclohexylalanine (AChxAla), and para-amino-methylphenylalanine (p-AMF). The procedures described by Nutt et al. are incorporated by reference.

Phenyl guanidines, benzyl guanidines, methylguanidines and N, N'-diethylguanidines are prepared from primary amines by general procedures well known in the art.

Trans-GuaChxAla, cis-GuaChxAla, trans-GuaChxGly and cis-GuaChxGly may be prepared by the following general procedure:

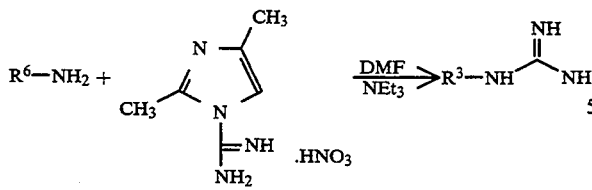

using reagent 3,5-dimethylpyrazole-1-carboxamidine nitrate, Methods of Enzymology 25b, 558 (1972).

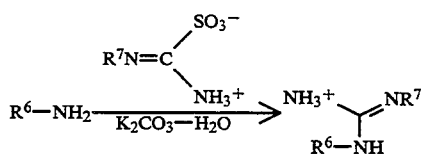

wherein $R^6$ is an alpha Boc-amino acid side chain or the side chain of an alpha amino acid in a peptide, and $R^7$ is alkyl, aryl, arylalkyl or cycloalkyl having 1–6 carbons, preferably cyclohexyl.

Alkyl- or aryl-iminomethane sulfonic acids are prepared by oxidation of the corresponding thioureas, as described in A. E. Miller and J. J. Bischoff *Synthesis*, pp. 777–779 (1986). Guanylation occurs in aqueous $K_2CO_3$, as described above. Alternatively, the reaction may be carried out in dimethylformamide-Et$_3$N (@pH 9). Reaction time is 24–48 hours in an aqueous system, and 3–20 hours in dimethylformamide.

Compounds of the invention may be prepared using solid phase peptide synthesis, such as that described by Merrifield, *J. Am. Chem. Soc.*, 85, 2149 (1964), although other equivalent chemical syntheses known in the art can also be used, such as the syntheses of Houghten, *Proc. Natl. Acad. Sci.*, 82, 5132 (1985). Solid-phase synthesis is commenced from the C-terminus of the peptide by coupling a protected amino acid to a suitable resin, as generally set forth in U.S. Pat. No. 4,244,946, issued Jan. 21, 1982 to Rivier et al., the disclosure of which is hereby incorporated by reference. Solution method can be used as described by Neurath et al. Chapter 2, pp. 106–253. Examples of synthesis of this general type are set forth in U.S. Pat. Nos. 4,305,872 and 4,316,891.

In synthesizing these polypeptides, the carboxyl terminal amino acid, having its alpha-amino group suitably protected, is covalently coupled to a chloromethylated polystyrene resin or the like. The chloromethylated polystyrene resin is composed of fine beads (20–70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin. After removal of the alpha-amino protecting group, as by using trifluoroacetic acid in methylene chloride, the amino protected derivative of the next amino acid in the sequence is added along with a condensation coupling agent such as dicyclohexylcarbodiimide. The remaining alpha-amino and side-chain-protected amino acids are then coupled by condensation stepwise in the desired order to obtain an intermediate compound connected to the resin.

The condensation between two amino acids, or an amino acid and a peptide, or a peptide and a peptide can be carried out according to the usual condensation methods such as azide method, mixed acid anhydride method, DCC (dicyclohexyl-carbodiimide) method, BOP (benzotriazole-1-yloxytris (dimethylamino) phosphonium hexafluorophosphate method, active ester method (p-nitrophenyl ester method, N-hydroxysuccinimido ester method, cyanomethyl ester method, etc.), Woodward reagent K method, carbonyldiimidazol method, oxidation-reduction method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, t-alkyloxycarbonylhydrazide resin an p-hydroxymethylphenylacetylamidomethyl resin (PAM).

Common to chemical syntheses of peptides is the protection of the reactive side-chain groups of the various amino acid moieties with suitable protecting groups at that site until the group is ultimately removed after the chain has been completely assembled. Also common is the protection of the alpha-amino group on a amino acid or a fragment while that entity reacts at the carboxyl group followed by the selective removal of the alpha-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the alpha- and omega-side chain amino groups are exemplified such as benzyloxycarbonyl (hereinafter abbreviated as Z), isonicotinyloxycarbonyl (iNOC), O-chlorobenzyloxycarbonyl [Z(2-Cl)], p-nitrobenzyloxycarbonyl [Z(NO$_2$)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc),9-fluorenylmethoxycarbonyl (Fmoc), methylsulfonylethoxycarbonyl (Msc), trifluoroacetyl, phthalyl, formyl, 2-nitrophenylsulphenyl diphenylphosphinothioyl (Ppt), dimethylphosphinothioyl (Mpt) and the like.

Protective groups for carboxy group include, for example, benzyl ester (OBzl), cyclohexyl ester (Chx) 4-nitrobenzyl ester (ONb), t-butyl ester (OBut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenylsulfonyl (Mts), and the like. The thiol group in cysteine may be protected with benzyl, p-methoxybenzyl, triphenylmethyl, acetylamidomethyl, ethylcarbamoyl, 4-methylbenzyl, 2,4,6-trimethylbenzyl (Tmb) etc., and the hydroxyl group in serine can be protected with benzyl, t-butyl, acetyl, tetrahydropyranyl etc.

Stewart and Young, "Solid Phase Peptide Synthesis:, Pierce Chemical Company, Rockford, Ill. (1984) provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151. These descriptions are hereby incorporated by reference.

After the desired amino-acid sequence has been completed, the intermediate peptide is removed from the resin support by treatment with a reagent, such as liquid HF, which not only cleaves the peptide from the resin, but also cleaves all the remaining protecting groups from the side chain which do not interfere in the cyclization reaction. Potentially reactive side chains functionalities are protected with blocking groups which are stable to HF. The peptides are cyclized by any one of several known procedures (see Schroder and Lubke, "The Peptides: Methods of Peptide Synthesis" Vol. I, Academic Press, New York (1965), pp. 271–286, the contents of which are hereby incorporated by reference), e.g. by forming a disulfide bridge between the cysteine residues using iodine in AcOH, or air oxidation at pH 8 in dilute NH$_4$OAc buffer. The polypeptide can then be purified by gel permeation chromatography followed by preparative HPLC, as described in Rivier et al., Peptides: Structure and Biological Function (1979) pp. 125–128.

EXAMPLE 1

Synthesis of aminomethylphenylalanine as α-BOC-Cbz-p-aminomethyl-D,L-phenylalanine for use in synthesis of Ac-Cys(Pmb)-Asn-Pro-(D,L-AMF(Cbz))-Gly-Asp(Bzl)-Cys-(Pmb)-OPam ®

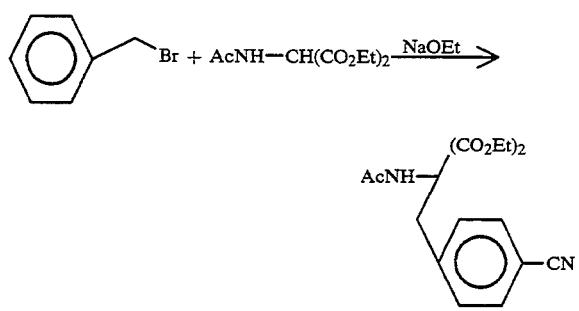

To 500 ml dry EtOH (4A sieves) was added 5.9 g Na (0.256 m) under nitrogen, 55.67 g (0.2563 m) of acetamido diethylmalonate and 50 g (0.2563 m) of p-cyanobenzylbromide, The mixture was heated to reflux which resulted in complete dissolution of starting materials and product. After 1 hour, the reaction solution was cooled, 1.5 liters of water was added and the precipitate was filtered to give 77.3 g of crude product which was recrystallized from 450 ml of EtOH to give 70.56 g of product (83% yield), mp 174.5°–175.5° C.; IR$_{CHCl_3}$ 2.97µ (NH), 5.78 (ester) 6.0 (amide) 4.52µ (CN) Rf (95-5-0.5-CHCl$_3$—MeOH—H$_2$O)=0.75 ppm NMR CDCl$_3$: 1.3 (t, CH$_3$CH$_2$O), 2.05 (s, CH$_3$C), 3.75 (s, ar—CH$_2$—C), 4.3 (m, CH$_3$CH$_2$—O) 6.5 (s, NH), 7.2 (d, arom), 7.6 (d, arom)

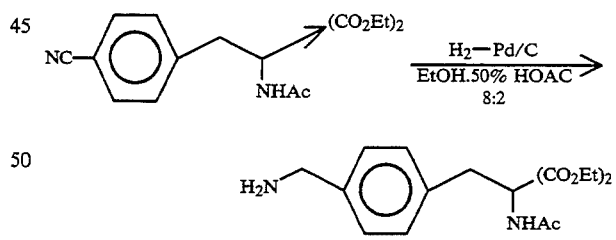

To a suspension of 20 g (60 mm) of p-CN-benzyl N-acetyl-diethylmalonate in 200 ml EtOH-50% HOAc (8:2) under a N$_2$ stream was added 4 g of 10% Pd/C and the mixture was treated with H$_2$ in a Parr Shaker for 70 minutes after which period 96% of theoretical amount of H$_2$ was consumed. The mixture was filtered through Celite, the filtrate was evaporated in vacuo to dryness to give a solid residue which was triturated with EtOAc, filtered and dried to give 21.45 g (90.2% yield) of product.

IR in CHCl$_3$ shows no CN at 4.5µ. RF (95-5-0.5 CHCl$_3$—MeOH-conc.NH$_4$OH)=0.3 (ninhydrin +) ppm NMR CH$_2$C @3.65 singlet, CH$_2$N @3.9 singlet CDCl$_3$

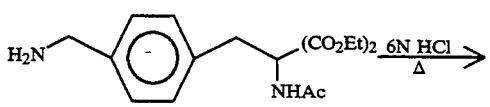

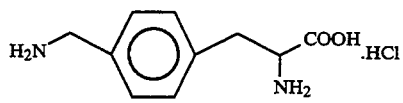

A solution of 21 g (53 mm) of N-acetyl diethyl ester p-aminomethylbenzyl aminomalonate in 100 ml of 6N HCl was refluxed for 24 hrs. The reaction solution was evaporated in vacuo to give 16.6 g of product as solid.
Rf (60-30-4-6, CHCl₃—MeOH—H₂O—NH₄OH)=0.15

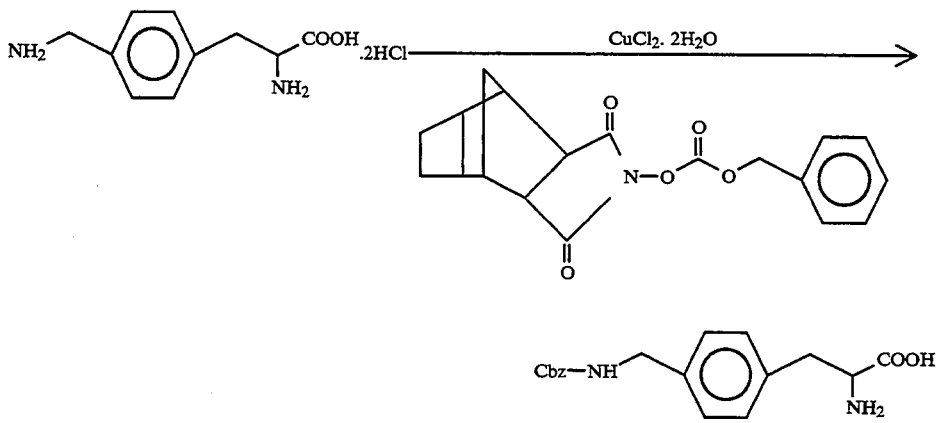

To all of p-aminomethylphenylalanine (53 mm) (prepared above) in 200 ml H₂O was added 4.92 g of CuCl₂.2H₂O. The mixture was adjusted to pH of 9 with NaOH. To the reaction mixture was added 18.26 g (58 mm) of the N-benzyloxycarbonyloxy-t-norbornene-2,3-dicarboximide reagent and the reaction mixture was kept at 5° C. for 18 hrs. The solid was filtered, washed with H₂O and EtOAc, and redissolved in HOAc and HCl to obtain a pH of 0.5. Upon standing, 9.5 g of product as the zwitterion precipitated. The filtrate was treated with H₂S, filtered through a pad of celite and pyridine was added to the filtrate to pH 6. The flocculent precipitate was filtered to give a second crop of product (1.5 g). Total yield was 11 g (58% yield). Anal. calcd. for C₁₈H₂₀N₂O₄

| calcd. | fd |
|---|---|
| N = 8.53 | 7.99 |
| C = 65.84 | 66.65 |
| H = 6.14 | 6.13 |

NMR in D₂O and NaOD evidenced product to have the Cbz group on the NH₂CH₂ and not the α-NH₂,

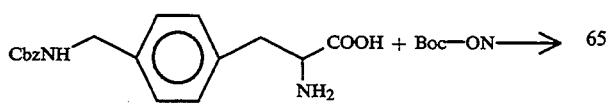

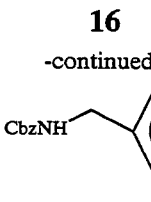

A suspension of 7.0 g (21.3 mm) of omega-Cbz-p-aminomethyl-DL-phenylalanine in 70 ml H₂O and 35 ml of THF was treated with 9.27 ml (63.9 mm) of NEt₃ and 5.51 g (22.36 mm) of Boc-ON (Aldrich) for 24 hrs during which time all starting material went into solution. To the reaction solution was added 150 ml of ethyl ether, the H₂O layer was separated and the ether layer was washed two times with H₂O; the combined H₂O layers were back-washed once with ether and acidified with citric acid to give a gummy solid. The aqueous supernatant was decanted, the gummy solid was extracted into EtOAc, the EtOAc solution was dried over MgSO₄, filtered and evaporated to a foamy residue (8.73 g). The crude product was crystallized from EtOAc-pet Et₂O to give 7.22 g (79.3% yield), m.p. 133°-133.5° C.

TLC Rf=0.35 (80-20-2, CHCl₃—MeOH—NH₄OH) NMR CD₃OD: 1.4(Boc), 2.9, 3.15 (m, β-CH₂), 4.25(s, CH₂N), 4.3 (m, α-H), 5.1(s,CH₂-Cbz) 7.2 ,7.3 (atom, Cbz,

EXAMPLE 2

Synthesis of Ac-Cys(Pmb)-Asn-Pro-[D,L-AMF(Cbz)]-Gly-Asp(Bzl)-Cys(Pmb)-OPam ®) and ultimately

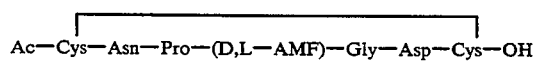

Starting with

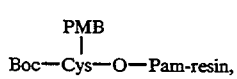

the alpha-amino Boc protecting group (tert-butylcarbonyl) is removed (while the Cys side-chain remains protected by p-methylbenzyl) using trifluoroacetic acid and methylene chloride, and the α-deprotected cysteine neutralized with diisopropylethyl amine. Boc-protected Asp (benzyl) (Asp (Bzl)) is then coupled to cysteine mediated by dicyclohexyl-carbodiimide, and deprotected with trifluoroacetic acid and methylene chloride. Asp is then neutralized with diisopropylethylamine. Following this stepwise procedure of coupling with dicyclohexylcarbodiimide, deprotection with trifluoroacetic acid and methylene chloride, and neutralization with diisopropylethylamine, Boc-protected Gly, AMF, Pro, Asn, Cys residues are coupled in succession. AMF is additionally protected by Cbz, (AMF (Cbz)), and the final Cys residue is again additionally protected by p-methylbenzyl. The final Cys is then acetylated with acetic anhydride.

Following acetylation, the following peptide-resin is formed:

Cleavage of the peptide from the resin is achieved using HF/anisole (9:1 (v/v)) to form:

A cyclic structure is formed by formation of a disulfide bridge between the cysteine residues. The peptide is dissolved in 50-80% AcOH:H₂O at room temperature, and the solution stirred during rapid addition of a solution of iodine in AcOH to a final concentration of 2.25 mg/ml of iodine. After I₂ hours reaction time, excess I2 and AcOH are removed by rotary evaporation under vacuum and the aqueous solution containing the cyclized peptide is purified using preparative HPLC in 0.1% TFA H₂O—CH₃CN gradient at which stage the D- and L-diastereomers are separated by conventional means. The final TFA salt product is converted to HOAc salt by passing through an ion exchange column BioRad AG3-X4A (acetate cycle). The finished peptide is:

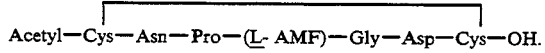

As an alternative to forming the disulfide bridge by iodine oxidation, the free SH peptide is dissolved in 1-5% HOAc at a concentration of approximately 2 mg/ml and the solution adjusted to approximately pH 7-8.5 with concentrated NH₄OH. Cyclization is accomplished under brisk stirring (preferably with a small piece of copper wire added to accelerate the reaction) during a period of 1-4 hours at 25°. The reaction mixture is then concentrated as before and product purified by preparative HPLC.

EXAMPLE 3

Synthesis of

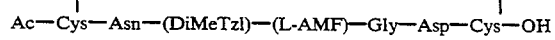

The same procedure for synthesizing the cyclic peptide of Example 2 is followed, except that Pro is replaced with DiMeTzl.

Therapeutic Utility

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Polypeptides of the invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol., 1987, 252: H, pp 615-621). Platelets released from artificial surfaces show impaired hemostatic function. Polypeptides of the invention may be administered to prevent adhesion.

Other applications of these polypeptides include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures. Polypeptides of the invention may also be used to prevent myocardial infarction.

These polypeptides may be administered by any convenient means which will result in its delivery into the blood stream in substantial amount including continuous intravenous or bolus injection or oral methods. Compositions of the invention include peptides of the invention and pharmacologically acceptable carriers, e.g. saline, at a pH level e.g. 7.4, suitable for achieving inhibition of platelet aggregation. They may be combined with thrombolytic agents such as plasminogen activators or streptokinase in order to inhibit platelet aggregation. They may also be combined with anticoagulants such as heparin, aspirin or warfarin. Intravenous administration is presently contemplated as the preferred administration route. They are soluble in water, and may therefore be effectively administered in solution.

In one exemplary application, a suitable amount of peptide is intravenously administered to a heart attack victim undergoing angioplasty. Administration occurs during or several minutes prior to angioplasty, and is in an amount sufficient to inhibit platelet aggregation, e.g. an amount which achieves a steady state plasma concentration of between about 0.05-30 μM per kilo, preferably between about 0.3-3 μM per kilo. When this amount is achieved, an infusion of between about 1-100 ηM per kilo per min., preferably between about 10-30 ηM per kilo per min. is maintained to inhibit platelet aggregation. Should the patient need to undergo bypass surgery, administration may be stopped immediately and will not cause complications during surgery that would be caused by other materials such as aspirin or monoclonal antibodies, the effects of which last hours after cessation of administration.

The present invention also includes a pharmaceutical composition comprising peptides of the present invention and tissue type plasminogen activator or streptokinase. The invention also includes a method for promoting thrombolysis and preventing reocclusion is a patient which comprises administering to the patient an effective amount of compositions of the invention.

The present invention may be embodied in other specific forms without departing from the spirit or essential attributes thereof. Thus, the specific examples described above should not be interpreted as limiting the scope of the present invention.

What is claimed is:

1. A compound selected from the group consisting of

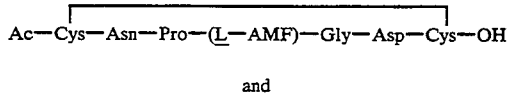

and

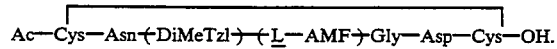

2. A compound of claim 1 which is

3. A compound of claim 1 which is

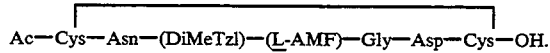

* * * * *